US010624810B2

(12) United States Patent
Hunter

(10) Patent No.: US 10,624,810 B2
(45) **Date of Patent: *Apr. 21, 2020**

(54) HANDS-FREE CRUTCH

(71) Applicant: iWALKFree, Inc., Mansfield (CA)

(72) Inventor: Bradly Hunter, Long Beach, CA (US)

(73) Assignee: IWALKFREE, INC., Long Beach, CA (US)

( * ) Notice: Subject to any disclaimer, the term of this patent is extended or adjusted under 35 U.S.C. 154(b) by 189 days.

This patent is subject to a terminal disclaimer.

(21) Appl. No.: 15/203,409

(22) Filed: Jul. 6, 2016

(65) Prior Publication Data

US 2016/0310345 A1 Oct. 27, 2016

Related U.S. Application Data

(63) Continuation of application No. 13/720,519, filed on Dec. 19, 2012, now Pat. No. 9,408,443.

(60) Provisional application No. 61/577,892, filed on Dec. 20, 2011.

(51) Int. Cl.

| | |
|---|---|
| ***A61F 2/60*** | (2006.01) |
| ***A61H 3/02*** | (2006.01) |
| ***A45B 3/00*** | (2006.01) |
| *A61H 3/00* | (2006.01) |

(52) U.S. Cl.

CPC ............. *A61H 3/0288* (2013.01); *A45B 3/00* (2013.01); *A61H 3/02* (2013.01); *A61H 2003/005* (2013.01); *A61H 2003/007* (2013.01); *A61H 2201/169* (2013.01)

(58) Field of Classification Search

CPC ........ A61F 2/60; A61H 3/02; A61H 2003/005

See application file for complete search history.

(56) References Cited

U.S. PATENT DOCUMENTS

| | | | |
|---|---|---|---|
| 1,185,906 | A | 6/1916 | Hoff |
| 2,242,748 | A | 5/1941 | Fulwiler |
| 2,678,054 | A | 5/1954 | Bostelman |
| 2,827,897 | A | 3/1958 | Pawlowski |
| 3,074,420 | A | 1/1963 | Gottman |
| 4,058,119 | A | 11/1977 | Rosequist |
| 4,291,715 | A | 9/1981 | Monte |
| 5,178,595 | A | 1/1993 | MacGregor |

(Continued)

FOREIGN PATENT DOCUMENTS

| | | | |
|---|---|---|---|
| CA | 2326678 | C | 11/2006 |
| CA | 2284952 | C | 2/2009 |

(Continued)

OTHER PUBLICATIONS

"Freedom Leg", weee.freedomlegbrace.com/how_it_works.html, screen capture Jul. 12, 2011.

*Primary Examiner* — Bruce E Snow

(74) *Attorney, Agent, or Firm* — Fish IP Law, LLP

(57) ABSTRACT

A crutch for assisting a user to walk includes a leg platform configured to support a portion of a leg of the user, and a ground contact having a weight supporting medial contact region that is disposed higher than a weight supporting lateral contact region. An optional strap on the leg platform can be used to maintain the leg in a forward position. An optional thigh saddle can be used to help prevent lateral movement of the user's upper thigh with respect to the crutch. An optional front facing handle can assist new users in learning to use the crutch.

8 Claims, 6 Drawing Sheets

(56) References Cited

U.S. PATENT DOCUMENTS

| | | | | |
|---|---|---|---|---|
| 5,300,016 | A | 4/1994 | Marlatt | |
| 5,575,299 | A | 11/1996 | Bieri | |
| 5,746,236 | A | 5/1998 | Tilsey et al. | |
| 6,494,919 | B1 | 12/2002 | Matthews | |
| 6,799,592 | B1 | 10/2004 | Reynolds | |
| 7,600,524 | B2 | 10/2009 | West | |
| 8,047,969 | B1 * | 11/2011 | Jay | A63B 25/10 482/75 |
| 8,778,031 | B1 | 7/2014 | Latour, Jr. et al. | |
| 2005/0109379 | A1 | 5/2005 | Rader | |
| 2007/0012345 | A1 | 1/2007 | Owens | |
| 2007/0251560 | A1 | 11/2007 | Moore | |
| 2011/0041884 | A1 | 2/2011 | Hanna et al. | |

FOREIGN PATENT DOCUMENTS

| | | | |
|---|---|---|---|
| DE | 69922935 | T2 | 4/2006 |
| DE | 10 2005 062 909 | A1 | 7/2007 |

* cited by examiner

FIG. 11B
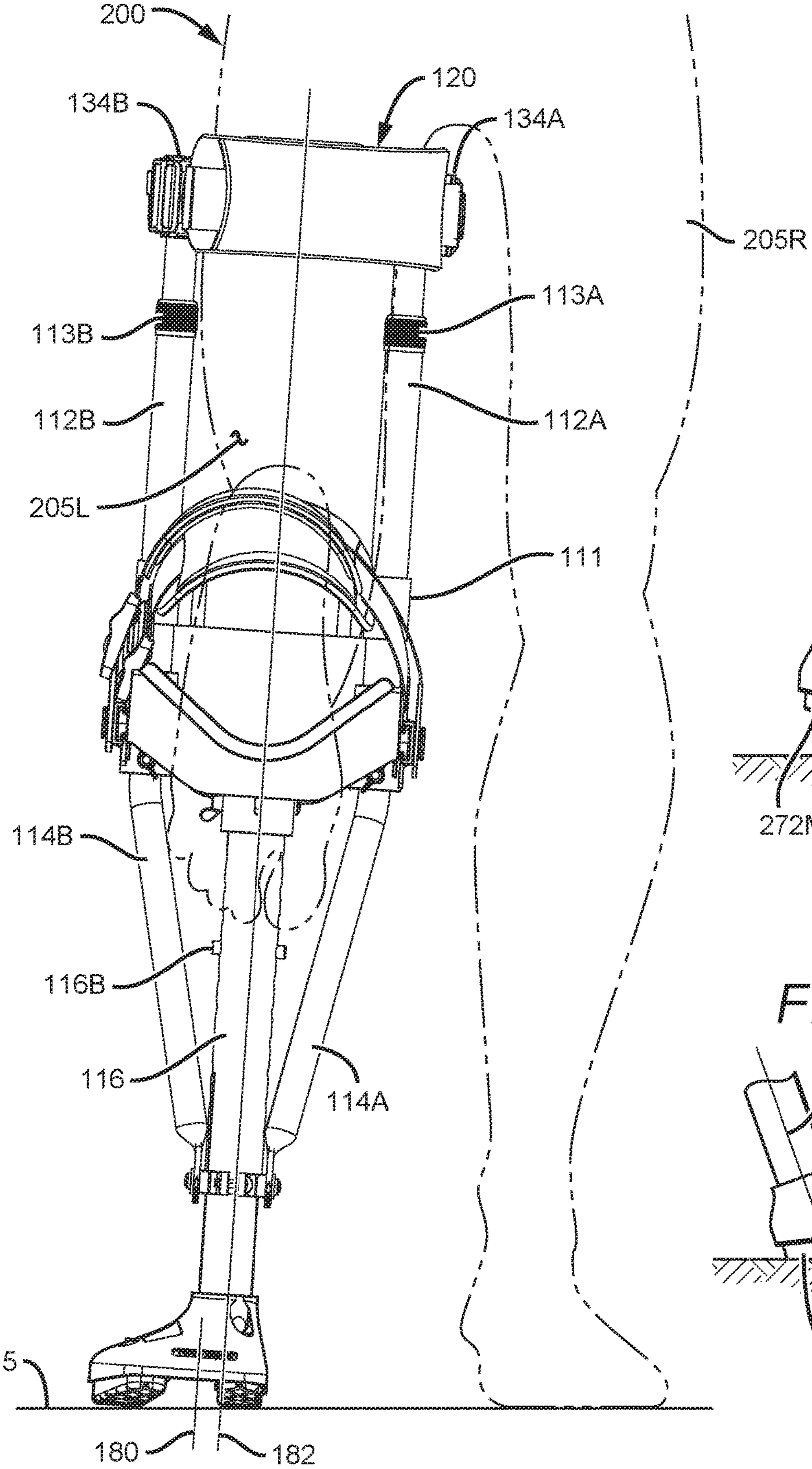
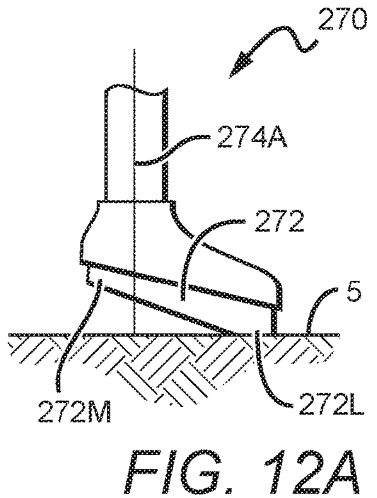
FIG. 12A
FIG. 12B
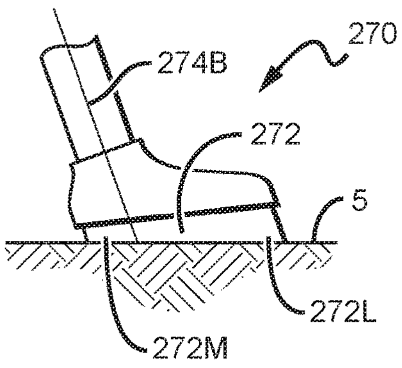

HANDS-FREE CRUTCH

This application is a continuation of U.S. application Ser. No. 13/720,519, filed Dec. 19, 2012, which claims priority to U.S. provisional application Ser. No. 61/577,892, filed Dec. 20, 2011. U.S. provisional application 61/577,892 and U.S. application Ser. No. 13/720,519 are incorporated herein in its entirety.

FIELD OF THE INVENTION

The field of the invention is crutches.

BACKGROUND

Numerous types of crutches are known for providing mobility to those who suffer from infirmities, injuries, and/or handicaps. Hands-free crutches are particularly useful because they allow their users to use both hands for tasks other than stabilizing the crutch.

The earliest hand-free crutches appear to have relied on monopods, i.e., a single ground contact pad that is substantially flat on the bottom. See e.g., U.S. Pat. No. 1,185,906 to Hoff (1916) and U.S. Pat. No. 2,827,897 to Pawlowki (1956). That strategy has persisted into the present, as exemplified by U.S. Pat. No. 3,074,420 to Gottman (1963), U.S. Pat. No. 4,058,119 to Rosequist (1977), U.S. Pat. No. 5,178,595 to MacGreggor (1993), U.S. Pat. No. 5,575,299 to Bieri (1996), U.S. Pat. No. 6,494,919 to Matthews (2002), and U.S. Pat. No. 7,600,524 to West (2009).

These and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

Starting in the mid-1990s three appears to have been recognition that a single foot was not satisfactory, and the field began experimenting with use of a second foot. See e.g., U.S. Pat. No. 5,746,236 to Tilsey (1998), U.S. Pat. No. 6,799,592 and Reynolds (2004). Other variations to improve stability have included a single foot having a width that extends from the medial to the lateral side of the user's foot, and even a three-footed crutch, see the Freedom Leg™ (2011) and US2007/0241560 to Moore (publ. 2007), respectively.

Unfortunately, these and all other known hands-free crutches are difficult to use due to lack of stability and/or lack of natural transfer of weight. The user must re-learn a new way of transferring weight to and from the crutch while walking. Thus, there is still a need for stable hands-free crutch, which allows the user to walk in a relatively natural manner.

SUMMARY OF THE INVENTION

The inventive subject matter provides apparatus, systems, and methods in which a hands-free knee crutch provides stable and natural weight transition by providing a ground support in which (1) a medial contact region is higher than a lateral contact region when weight is being transmitted vertically to the ground or other surface, and (2) both the medial and lateral contact regions touch the surface when weight is being transmitted to the surface at some functional angle off vertical.

The medial and lateral contact regions can be positioned on one or more feet, but are preferably positioned on a single foot. Since the ground support is slightly supinated, the foot or feet is/are preferable rotatable relative to the knee platform to accommodate either left or right leg usage. The foot (or lateral foot where there are two feet) also preferably has a symmetrically curved lateral edge.

In especially preferred embodiments the medial and lateral contact regions are disposed on medial and lateral pads, respectively, which can advantageously be configured as sagitally oriented rockers. In a rocker configuration, anterior and posterior ends of the pads are curved upwards relative to the middle. Pads can be part of a unitary whole, but are preferably separate components, separated by at least 5 mm, more preferably at least 1 cm, more preferably at least 2 cm, more preferably at least 3 cm, more preferably at least 4 cm, and most preferably at least 5 cm. Even wider separations are also contemplated, depending in part on the width of the foot and the width of the pads. The pads and/or treads on the pads can be user replaceable.

The extent to which the medial contact region can be higher than the lateral portion when weight is being transmitted vertically to the surface is between 1 mm and 10 mm, more preferably between 2 mm and 5 mm, and most preferably between 3 mm and 5 mm. In some contemplated embodiments that difference can be adjusted by the user.

Preferred leg supports are significantly different from others on the market. In one aspect the leg platform can have a posteriorly narrowing "V" or "U" shaped support. In another aspect, preferred crutches include a knee fastener that pulls the knee anteriorly and inferiorly. In another aspect, preferred crutches include a thigh fastener that couples to an at least partially rigid thigh contact, which provides additional lateral support and alignment of the frame. Most preferably the thigh contact is part of an upper thigh saddle having both inner and outer thigh contacts. As used herein a "knee strap" is a knee fastener that pulls the knee anteriorly and inferiorly.

In addition to the usual strap and height adjustments, preferred embodiments include: (1) adjustment for the thigh saddle or other contact; (2) relative height adjustments for the medial and lateral contact regions of the foot or feet; and (3) replaceable treads on medial and lateral pads of the foot or feet.

Various objects, features, aspects and advantages of the inventive subject matter will become more apparent from the following detailed description of preferred embodiments, along with the accompanying drawing figures in which like numerals represent like components.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

BRIEF DESCRIPTION OF THE DRAWING

Prior art

Prior art

Prior art

Prior art

FIG. 11B is a rear view of a person using the crutch of FIGS. 5-9 to support his left leg, where weight is being transmitted vertically and an angle off vertical with respect to the ground.

FIG. 12A is a vertical, coronal cross-section of a foot, viewed from behind when the crutch is used to support a right leg, in accordance with some aspects of the inventive subject matter, in which weight is being transmitted vertically to the ground.

FIG. 12B is a vertical, coronal cross-section of the foot of FIG. 12A, in which the weight is being transmitted to the ground at an angle of about 1-5° off vertical.

DETAILED DESCRIPTION

The prior art failed to appreciate a critical feature of crutches; that when used by the average person, weight passing through the supported leg will generally be directed off vertical. The current inventor took that one step further, recognizing that the foot (or feet) of a crutch should therefore have a medial contact region that is raised relative to a lateral contact region when weight is being transmitted vertically to the ground or other horizontal surface. These distinctions are readily apparent by viewing FIGS. 1A-3B.

Figure 1A:
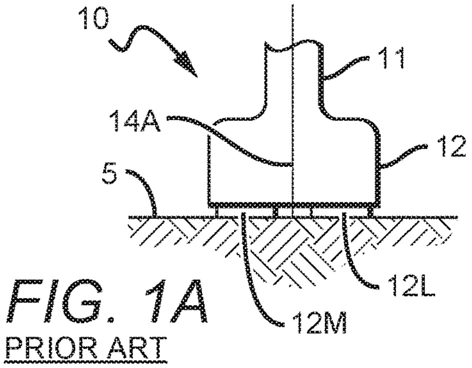
FIG. 1A PRIOR ART
FIG. 1A is a vertical, coronal cross-section of a flat-bottomed foot of a hands-free crutch, viewed from behind when the crutch is used to support a right leg, in which weight from the user is being transmitted vertically to the ground.

In FIG. 1A a flat-bottomed foot 12 of a lower portion of hands-free crutch 10, is pushing against the ground 5. The weight of a user (not shown) is being transmitted vertically through a post 11 to the ground 5 as shown by force line 14A. Assuming this crutch is being used on a right leg, then viewed from the rear there is a medial contact region 12M on the left and a lateral contact region 12L on the right, coupled together to form a single pad. Medial contact region 12M and lateral contact potion 12L contact the ground 5 at the same time.

Figure 1B:
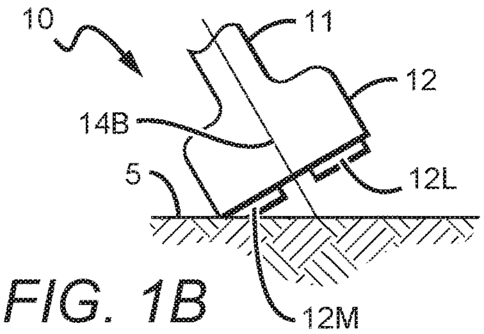
FIG. 1B PRIOR ART
FIG. 1B is a vertical, coronal cross-section of the flat-bottomed foot of FIG. 1A, in which the weight is being transmitted to the ground at an angle of about 1-5° off vertical.

In FIG. 1B the flat-bottomed foot 12 of FIG. 1A is pushing against the ground 5 at an angle shown by force line 14B. Here the medial contact region 12M is touching the ground 5, but the lateral contact region 12L is off the ground 5.

Figure 2A:
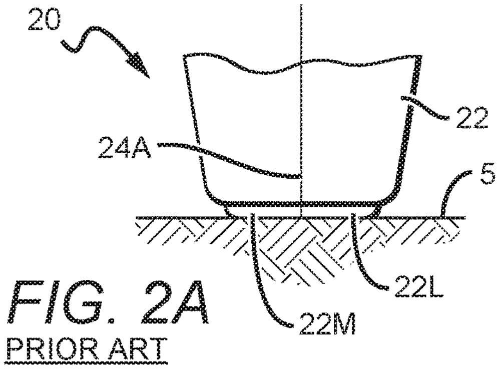
FIG. 2A PRIOR ART
FIG. 2A is a vertical, coronal cross-section of a rounded, conventional crutch foot tip, viewed from behind when the crutch is used to support a right leg, in which weight from the user is being transmitted vertically to the ground.

A similar situation occurs with a rounded foot. In FIG. 2A a rounded, conventional crutch foot 22 of a lower portion of a crutch 20, is pushing against the ground 5. Since the rounded foot has some flexibility, and assuming this crutch is being used on a right leg, there is still a medial contact region 22M and a lateral contact region 22L. The weight of a user (not shown) is being transmitted vertically to the ground 5 as shown by force line 24A. Here, the medial contact region 22M and lateral contact region 22L are contacting the ground 5 at the same time.

Figure 2B:
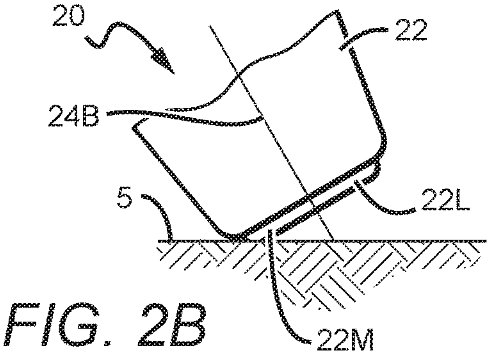
FIG. 2B PRIOR ART
FIG. 2B is a vertical, coronal cross-section of the rounded, conventional crutch foot tip of FIG. 2A, in which the weight is being transmitted to the ground at an angle of about 1-5° off vertical.

In FIG. 2B the rounded, conventional crutch foot tip 22 of FIG. 2A is pushing against the ground 5 at an angle shown by force line 24B. Here the medial contact region 22M is touching the ground 5, but the lateral contact region 22L is off the ground 5.

Figure 3A:
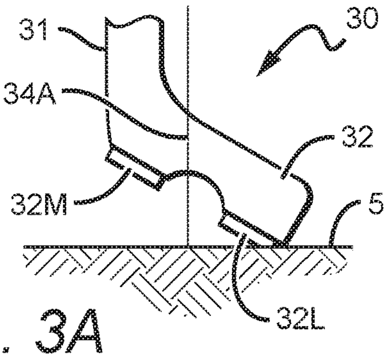
FIG. 3A is a vertical, coronal cross-section of a foot, viewed from behind when the crutch is used to support a right leg, in accordance with some aspects of the inventive subject matter, in which weight is being transmitted vertically to the ground.

In an embodiment of FIG. 3A according the inventive subject matter herein, foot 32 of the lower portion of hands-free crutch 30, is pushing against the ground 5. The weight of a user (not shown) is being transmitted vertically to the ground 5 as shown by force line 34A. Assuming this crutch is being used on a right foot, there is a lateral contact region 32L that is touching the ground, and a medial contact region 32M that is currently raised above the ground 5.

Figure 3B:
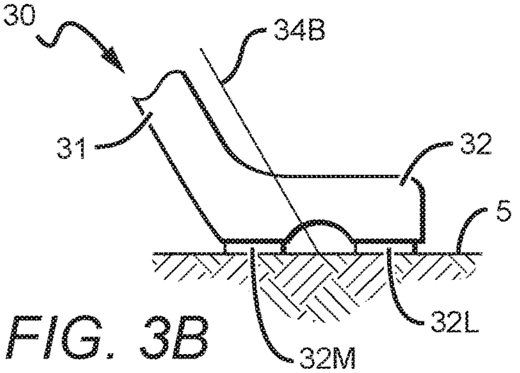
FIG. 3B is a vertical, coronal cross-section of the foot of FIG. 3A, in which the weight is being transmitted to the ground at an angle of about 1-5° off vertical.

In FIG. 3B the foot 32 of FIG. 3A is pushing against the ground 5 at an angle shown by force line 34B. Here both the medial contact region 32M and the lateral contact region 32L are touching the ground 5 at the same time.

Figure 4A:
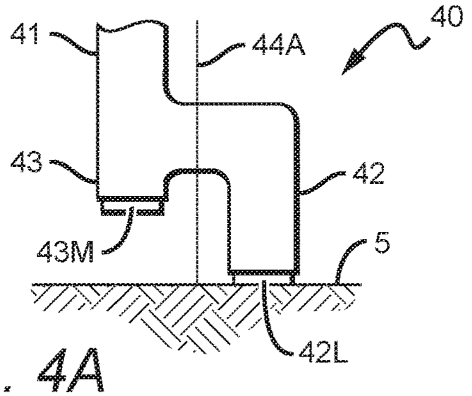
FIG. 4A is a vertical, coronal cross-section of an alternative design having two feet, in which weight is being transmitted vertically to the ground.
Figure 4B:
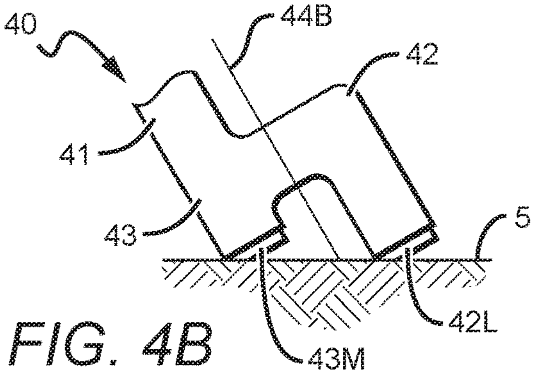
FIG. 4B is a vertical, coronal cross-section of the foot of FIG. 4A, in which the weight is being transmitted to the ground at an angle of about 1-5° off vertical.
Figure 6:
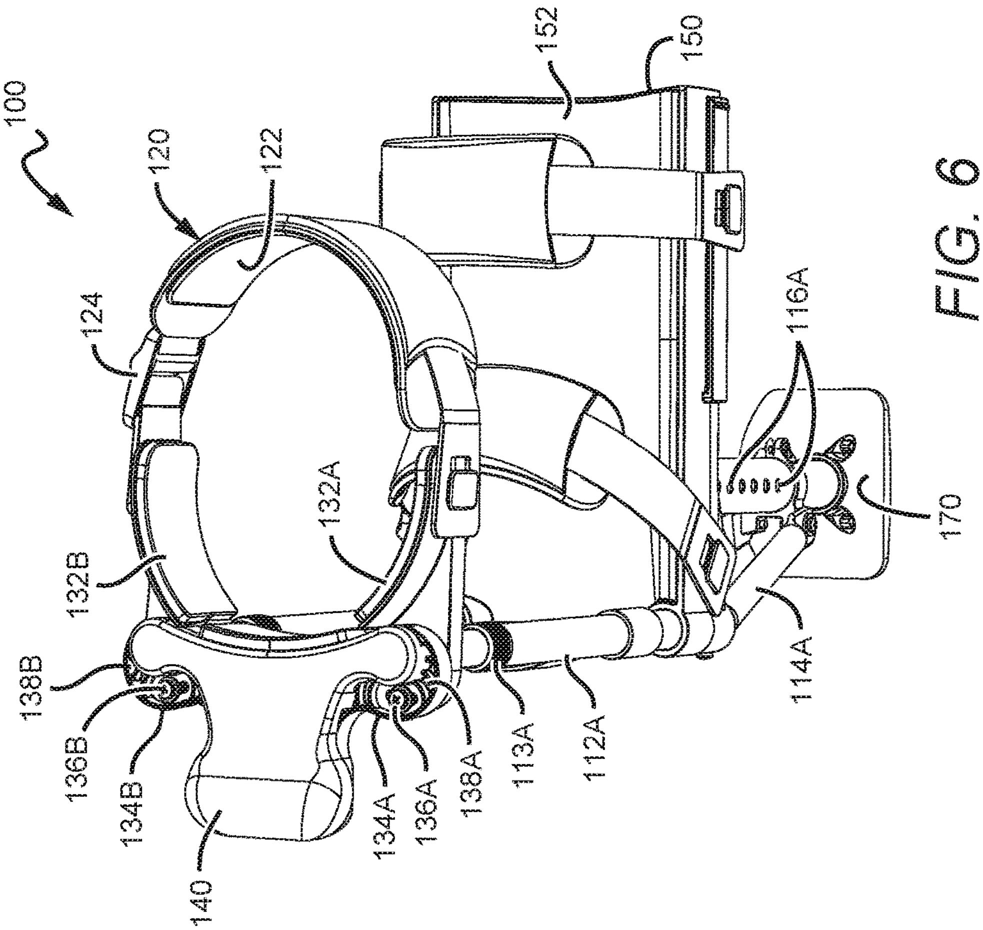
FIGS. 5-8 are perspective views of a crutch according to the inventive subject matter, in which the foot is oriented for use in supporting a right leg.
Figure 5:
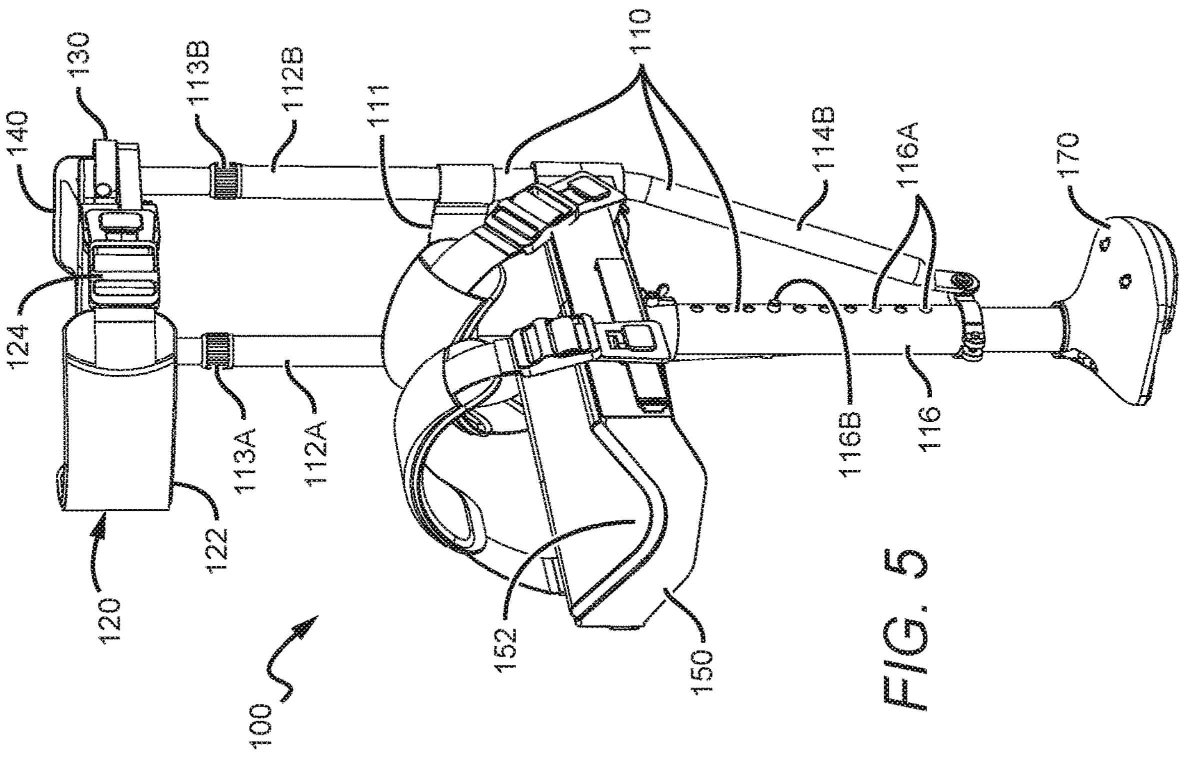
Figure 8:
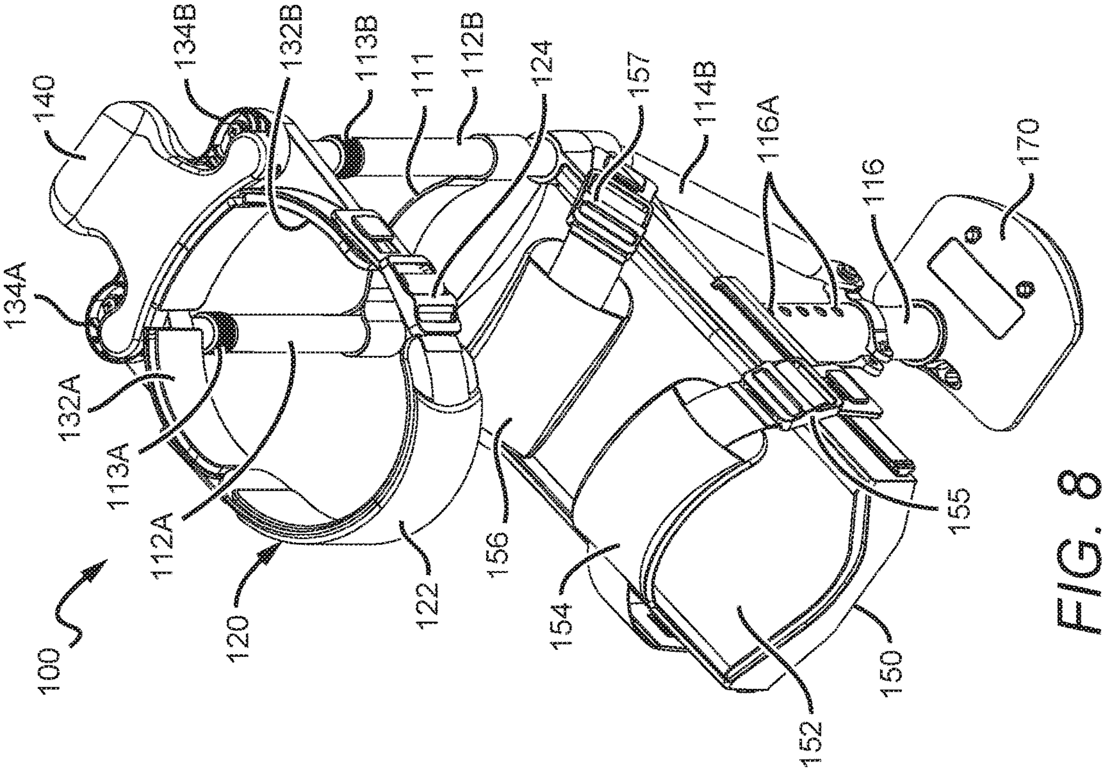
Figure 7:
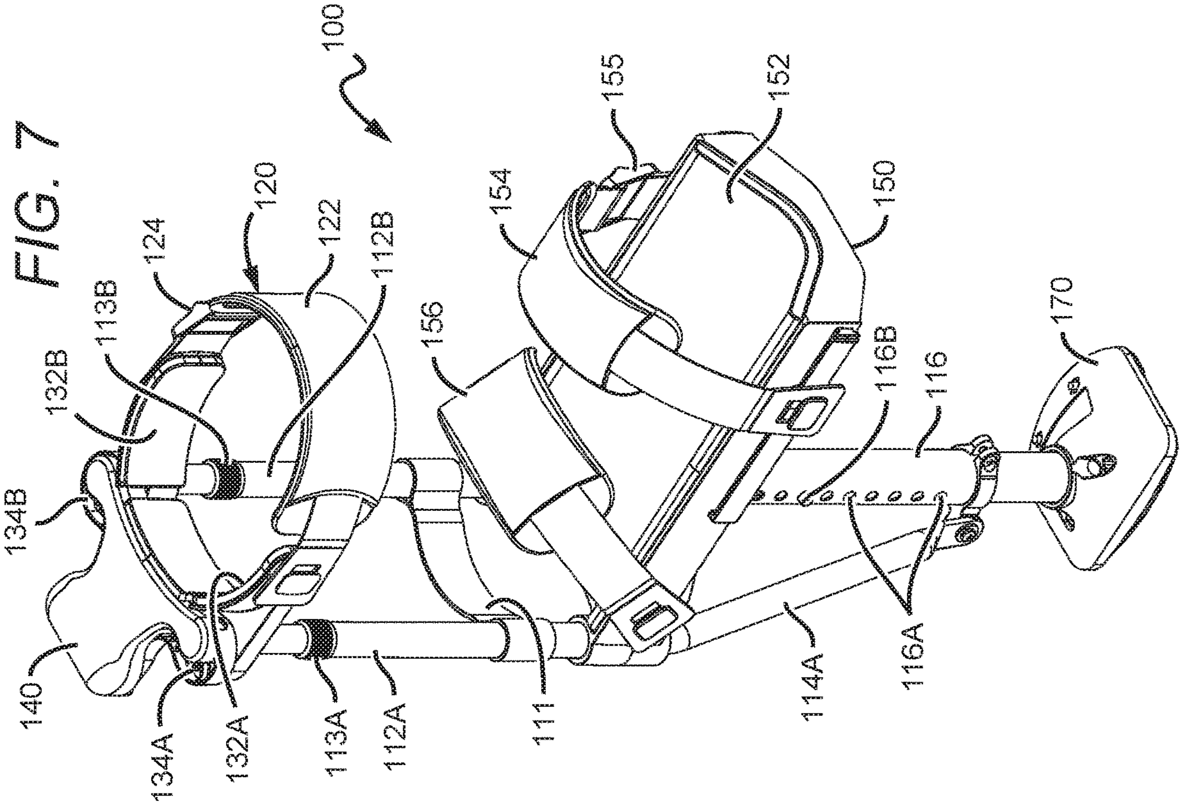

FIGS. 4A and 4B are similar to FIGS. 3A and 3B, except that here the lower portion of hands-free crutch 40 has two feet 42 and 43. Assuming this crutch is being used to support a user's right leg (not shown), the lateral contact region 42L is on the right of foot 42, and the medial contact region 43M is on the left foot 43. In FIG. 4A the force line 44A is vertical, and the medial contact region 43M is elevated while the lateral contact region 42L is touching the ground. In FIG. 4B the force line 44B is at an angle off vertical, so that both the lateral contact region 42L and the medial contact region 43M are touching the ground 5 at the same time.

The minimum angle off vertical at which both lateral and medial contact regions will touch the ground is referred to herein from time to time as the critical angle, and will depend on how several factors, including far apart the two weight bearing pads (or feet) are located, and the relative height of the more medial one when the force line is vertical. Contemplated critical angles include 1-2°, 2-3°, 3-4° and 4-5°. In general, the critical angle will be between 1° and 5°, although both lesser and greater angles are contemplated.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention. Unless otherwise expressly stated, all ranges include their endpoints.

As shown in FIGS. 3B and 4B, the medial ground contact region acts as a counter-balance to the lateral ground contact region. In general, the greater distance between the medial and lateral ground contact regions, the higher the medial ground contact region should be above the lateral ground contact region. And yet, these distances should not be very great. If user is walking with the crutch using a slight abduction, then simultaneous ground contact will occur with each step unless the user missteps.

Although two ground contact regions seems to work the best, it should be appreciated that one could have more than two such regions. In addition, the total are of all regions of ground contact can be fairly large. In preferred embodiments that total is at least 50 $mm^2$, more preferably at least 75 $mm^2$, more preferably at least 100 $mm^2$, and in some embodiments at least 125 $mm^2$. FIGS. 3A, 3B, 3C and 3D should be interpreted as having a total area of ground contact of at least 125 $mm^2$.

In FIGS. 5-8 a crutch 100 generally comprises a frame 110, to which are coupled a thigh fastener 120, a thigh saddle 130, a handle 140, a leg platform 150, and a foot 170.

The frame 110 generally comprises two upper supports 112A, 112B, two lower supports 114A, 114B, and a post 116. The thigh fastener 120, thigh saddle 130, handle 140 and leg platform 150 are all connected directly to the two upper supports 112A, 112B. The post 116 is connected to the leg platform 150, the lower supports 114A, 114B and the foot 170. The frame members are preferably aluminum to provide sufficient strength with relatively low weight. All suitable materials are also contemplated, including steel, composites, rigid plastics, which could be extruded to include an internal I-beam for strength.

The two upper supports 112A, 112B are preferably telescoping, and include locks 113A and 113B, respectively. The thigh fastener 120 preferably comprises a plastic, including for example nylon or polyester webbing, or other strap 122, which can be tightened at fastener 124.

The thigh saddle 130 generally comprises a left arm 132A and a right arm 132B, which are at least partially rigid, and extend out from mechanisms 134A and 134B respectively. Those mechanisms force the arms to extend either more directly backwards above the leg platform 150 to accommodate a relatively narrow thigh, or further apart from each other to accommodate a relatively wider thigh. Because of their rigidity, the left and right arms 132A, 132B help stabilize the crutch 100 relative to the thigh. In preferred embodiments, the arms can be adjusted independently, allowing proper vertical alignment of the crutch for a wide range of leg geometries. The mechanisms 134A, 134B can be any suitable mechanisms for achieving the purposes described herein, an in the relevant figures are merely screws 136A, 136B that tighten ratchet teeth (only partially shown as 138A, 138B) against one another.

It should also be appreciated that much of the stabilization provided by thigh saddle 130 can be provided by an at least partially rigid inner thigh arm operating by itself, i.e., without cooperation of a lateral arm.

Lateral adjustability of the inner thigh member should be interpreted as adjustability relative to the leg platform, and can be accomplished in many different ways. One way is to provide rotation of the inner thigh member using a mechanism as shown in FIGS. 5-8. Another way is to provide an inner thigh member that is telescoping, or has an extension. Another way is to provide replaceable inner thigh members of different geometries. Another way is to support the inner thigh member on a carriage with transverse adjustments. Still another way is to provide a frame mount of the inner thigh member that is adjustable. Still another way is provide the leg platform with lateral mobility.

The same adjustment mechanisms could apply to an outer thigh member.

As used herein, the term "at least partially rigid" with respect to an object means that a 5 cm length of the object cannot be bent under normal operating conditions (STP) by more than 2 cm without permanently deforming the object.

Although not shown in the Figures, an alternative thigh saddle could move laterally relative to the frame. The key is that no matter how the thigh saddle is structured, it should have sufficient rigidity to constrain crutch movement at the upper thigh, yet can be adjustable to have proper placement on thighs of different sizes and shapes.

Handle 140 is also preferably stiff plastic, but could also be wood, metal or some other material. Experiments have shown that handle 140 is important for some new users to gain confidence in using the device. However, due to the many other novel features discussed herein, most new users find the handle unnecessary after only a few minutes of practice. The handle can also be used for short trips when the user does not want to take time to strap in, and for long trips to combat leg fatigue.

As shown, handle 140 is positioned medially relative to a front perspective of the frame, rather than being placed on one side of the frame as in prior art devices. Medial positioning is considered herein to be advantageous because it facilitates use in standing up from a seated position, and facilitates use of the crutch as a cane. Although a handle need not be placed exactly in a medial sagittal line of the crutch, it is preferred that the handle be positioned such that a medial sagittal plane of the crutch passes through at least a portion of the handle. As used herein, the medial sagittal plane of a crutch is to be taken as the vertical plane that passes through the leg platform along a user's lower leg when the leg is fastened into the crutch for walking.

In the crutch of claim 22, the top of the handle is positioned at an approximate top of the frame. This is also not an absolute requirement. It is, however, preferred that the top of the handle be positioned within 10 cm of the top of the frame, more preferred that the top of the handle be positioned within 5 cm of the top of the frame, and most preferred that the top of the handle be positioned within 2 cm of the top of the frame.

Contemplated handles need not have any particular ergonomic shape. Contemplated handles include padded bars as show in FIGS. 6, 7, 8, and 9, as well as more knob shaped handles (not shown). Contemplated handles may or may not be padded, and may or may not have a leather or other coating.

In FIGS. 6, 7, 8, and 9, the handle should be interpreted as being integral with the thigh saddle.

Leg platform 150 has a support 152 sized and dimensioned to receive one of the lower legs of the user, with the knee facing forward and the user's foot facing rearward. Since the knee of many people is wider than the anterior (bony) portion of the lower leg, the knee (forward) portion of the support 152 is wider than the more rearward portion of the cushion 152. Further, as the support transitions from anterior to posterior, the U shape similarly transitions to more of a V shape to better conform to the contours of the human leg. This provides additional proprioception, stability and control of the crutch.

A rear strap 154 and rear fastener 155 keep the mid portion of the user's lower leg snug against the cushion 152, while a forward strap 156 and forward fastener 157 keep the upper portion of the user's lower leg snug against the cushion 152. The forward strap 156 is preferably coupled to the leg platform 150 quite close to the upper supports 112A, 112B, such that the strap can actually contact the user's leg at or near the popliteal fossa, and tend to pull the leg down against both the cushion 152 and forward against a blocking band 111 configured between the two upper supports 112A, 112B. The blocking band 111 stops the knee from pushing forward in the space between the two upper supports 112A, 112B.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

Post 116 is preferably telescopic, with holes 116A and at least one pin 116B to maintain a desired relationship between the moving telescoping parts. Adjustment of the effective length of post 116 allows for operation of the crutch 100 with users having very different leg lengths.

Figure 9:
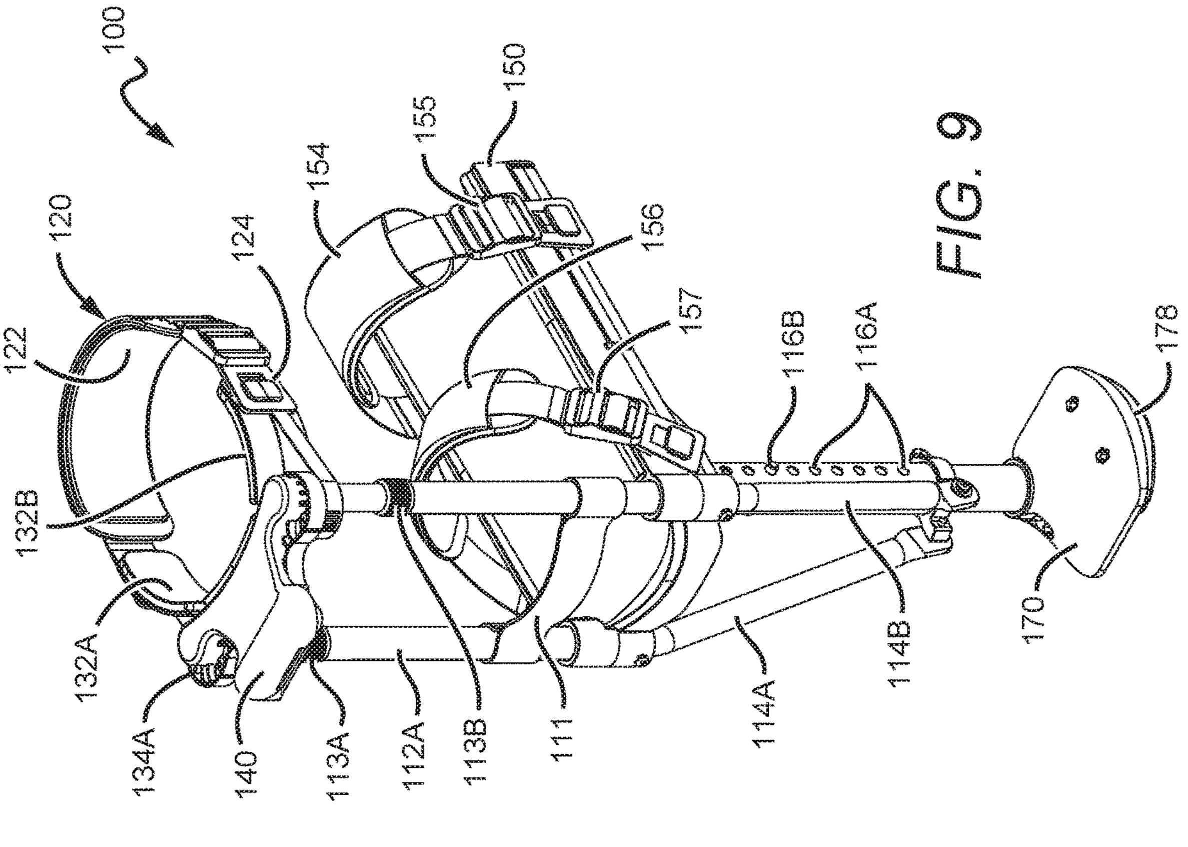
FIG. 9 is a perspective view of the crutch of FIGS. 5-8, in which the foot is oriented for use in supporting a left leg.

FIG. 9 is a perspective view of the crutch of FIGS. 5-8, in which the foot is oriented for use in supporting a left leg.

Figure 10:
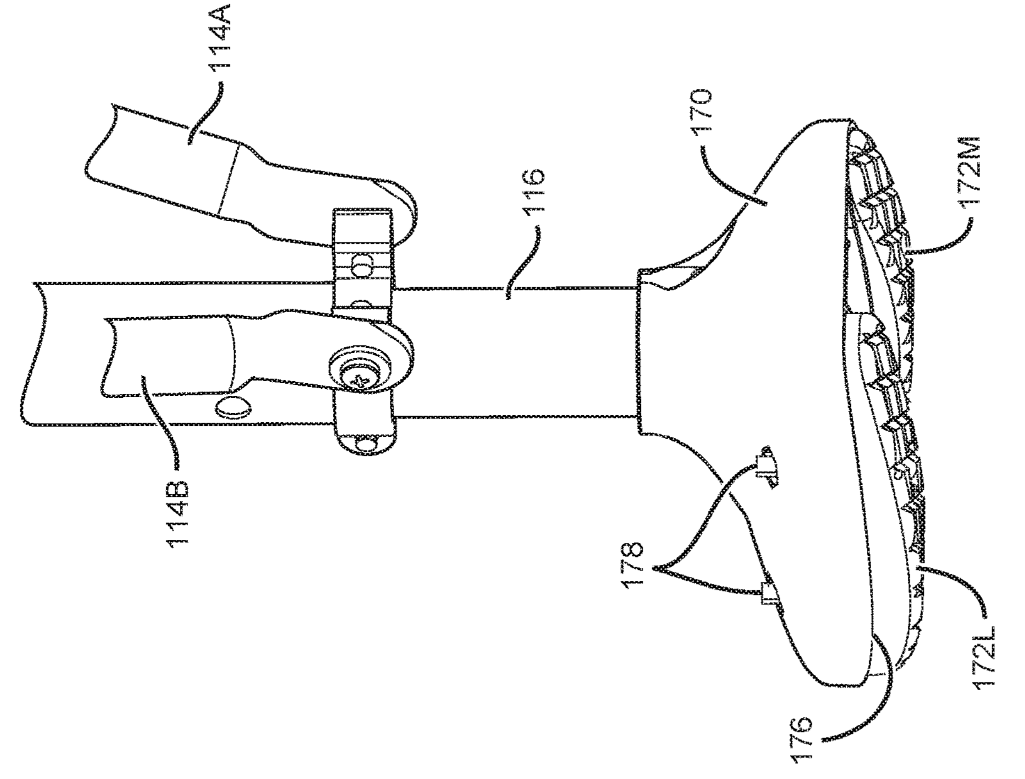
FIG. 10 a perspective view of the foot of the crutch of FIGS. 5-9.

Foot 170 is as described above with respect to FIGS. 3A and 3B, and shown in FIGS. 5-9. However, as perhaps more clearly seen in FIG. 10, foot 170 has two pads 172L and 172M that correspond to the medial and lateral contact regions, respectively. Each of the pads 172L, 172M is has a rocker configuration, having a convexity facing the floor or other surface, and oriented to rock in an at least approximately sagittal direction. In this particular embodiment the pads 172L, 172M have user replaceable treads 174L, 174M. Any suitable mechanism can be used to ensure that the bottom of the more medial pad 172M is raised relative to the bottom of the more lateral pad 172L, including a shim 176, placed above the more lateral pad 172L. Relative height can also be adjusted using adjusting screws 178.

The two pads 172L and 172M are preferably spaced apart by a distance X. X is preferably between 5 mm and 100 mm, more preferably between 40 mm and 80 mm, and most preferably between 60 mm and 80 mm. Since the pads 172L and 172M each have width, the distance between the pads is taken between the centers of the bottom-most regions of each of the pads when the user's weight is directed vertically downward. Where one or more pads are curved, there are of course multiple centers, and the distance between the pads is taken between the furthest apart centers.

Foot 170 can be oriented for use with support of a user's left or right foot merely by rotating the foot 180° relative to the post 116, or rotating both the foot 170 and an inner portion of the post 116 relative to the leg platform 150. To that end foot 170 has a curved lateral edge 178, with symmetry such that the foot 170 works equally well, and looks similar, in both left leg and right leg configurations.

Figure 11A:
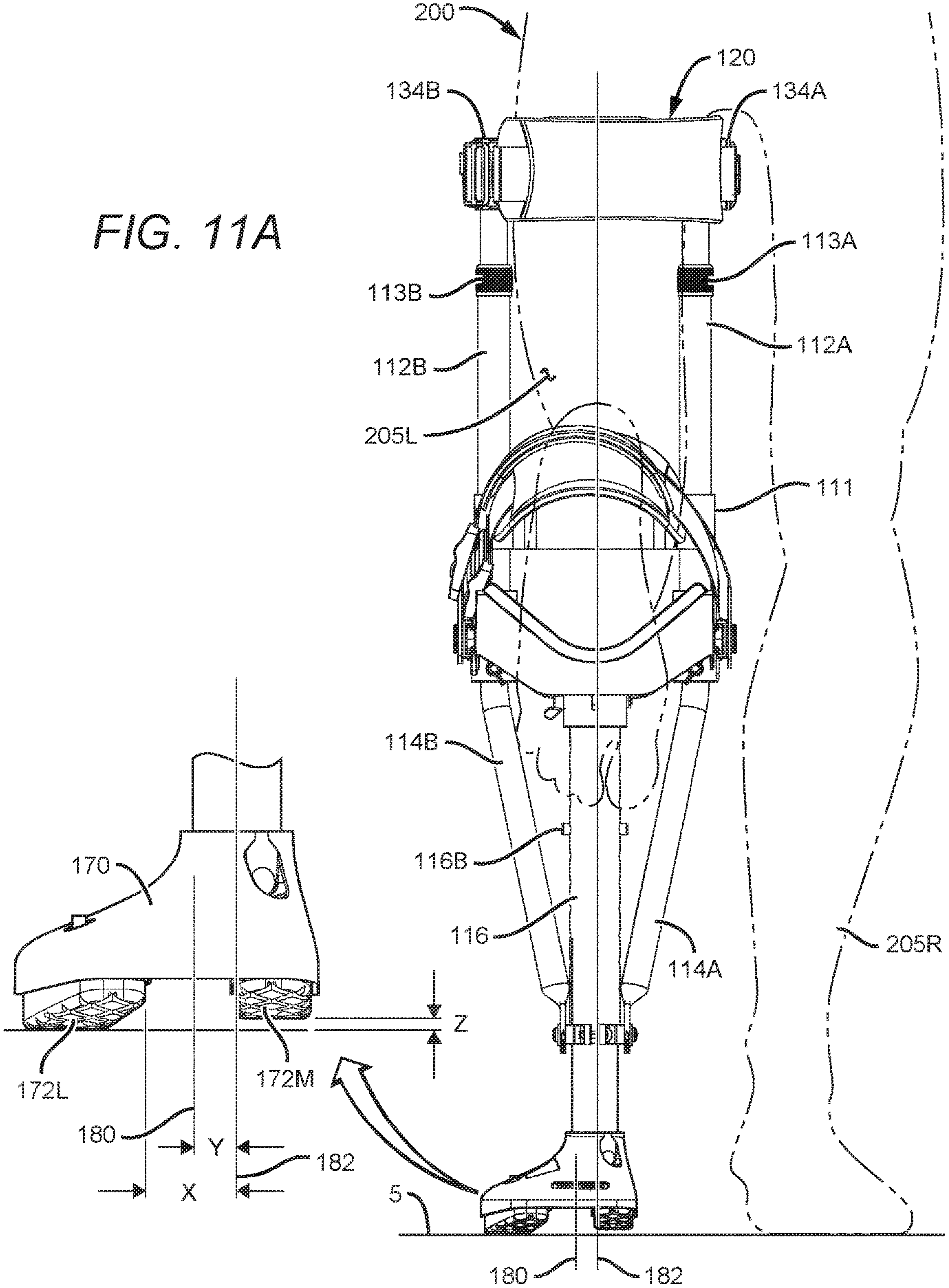
FIG. 11A is a rear view of a person using the crutch of FIGS. 5-9 to support his left leg, where weight is being transmitted vertically to the ground.

FIG. 11A is a rear view of a person 200 having a left leg 205L and a right leg 105R. In this example the person is using the crutch of FIGS. 4-8 to support his left leg 205R, where the user's weight is being transmitted vertically to the ground. FIG. 11B is a rear view of a person using the crutch of FIGS. 4-8 to support his left leg, where the user's weight is being transmitted at an angle off vertical.

Two additional features are readily apparent from FIGS. 11A and 11B. First, in FIG. 11A, where the user's weight is pushing vertically down against the ground or other surface 5, a median sagittal vertical plane 180 between the medial and lateral contact regions (in this case medial contact region 172L and 172M) is laterally positioned from a median sagittal vertical plane 182 of the leg platform 150 by an offset Y of at least 1 mm. Y is preferably at least 1 mm, more preferably at least 5 mm, but not more than 10 mm. Here again, since the pads 172L and 172M each have width, the median between the pads is taken between the centers of the bottom-most regions of each of the pads when the user's weight is directed vertically downward.

Second, in FIG. 11A the medial contact region 172M and is raised relative to the lateral contact region 172L by a distance Z. Z is preferably at least 1 mm, more preferably at least 2 mm, but not more than 10 mm. The lateral contact region 172L is touching the ground.

FIGS. 12A and 12B show yet another embodiment, in which a crutch has a foot 270 with only a single ground contact region 272. In these instances the bottom 272 of the foot has a proper camber to accommodate abduction of the user's supported leg, and what could be considered the lateral ground contact region 272L is continuous with the medial ground contact region 272M. When applying the claims to this type of embodiment, the height difference between medial ground contact region and the lateral ground contact region, and the separation between those regions, should be calculated using the medial most edge of the bottom 272M and the lateral most edge of bottom 272L.

Astute readers will appreciate that as with other figures, FIGS. 12A and 12B depict the height of medial ground contact portion 272M relative to the lateral ground contact 272L, and the angles at which force lines are directed to the ground 5, in an exaggerated fashion for ease of viewing, and should be interpreted according to the angles given in the specification. More accurate representations are shown in FIGS. 11A and 11B. Force line 274A should be interpreted as being vertical.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A crutch configured to accommodate different circumference legs, comprising:

a frame;

a lower leg platform coupled to the frame;

a thigh fastener coupled to the frame through left and right arms, the left and right arms disposed to engage a user's upper thigh; and independently adjustable left and right mechanisms configured to adjustably fix the angular positions at which the left and right arms, respectively, extend from the frame along a horizontal plane such that the angular positions of each of the left and right arms can be fixed at a plurality of angles along the horizontal plane relative to the frame and such that the angular positions of each of the left and right arms relative to the frame along the horizontal plane can be fixed at different angles from each other.

2. The crutch of claim 1, wherein at least one of the left and right arms is at least partially rigid.

3. The crutch of claim 2, wherein at least one of the left and right arms has a length of at least 4 cm.

4. The crutch of claim 1, wherein the lower leg platform transitions from a more “U” shaped anterior portion to a more “V” shaped posterior portion.

5. The crutch of claim 1, further comprising a forward fastener positioned to draw the user’s knee anteriorly and inferiorly.

6. The crutch of claim 1, further comprising a rear fastener configured to fasten a mid portion of the user’s lower leg to the lower leg platform.

7. The crutch of claim 1, further comprising a foot rotatable relative to the frame.

8. The crutch of claim 1, further comprising a foot rotatable with respect to the lower leg platform.

* * * * *